«12» United States Patent [19]
Kaneyoshi et al.

[11] Patent Number: 5,644,037
[45] Date of Patent: Jul. 1, 1997

[54] METHOD FOR THE PREPARATION OF POLYHEDRAL PARTICLES OF A RARE EARTH AMMONIUM DOUBLE OXALATE

[75] Inventors: Masami Kaneyoshi; Isamu Fujioka; Shigeru Sakai, all of Fukui-ken, Japan

[73] Assignee: Shin-Etsu Chemical Co., Ltd., Tokyo, Japan

[21] Appl. No.: 433,925

[22] Filed: May 2, 1995

[30] Foreign Application Priority Data

May 18, 1994 [JP] Japan .................... 6-103747

[51] Int. Cl.$^6$ .................... C07F 5/00; C04B 35/58; C01F 17/00; C09K 11/08
[52] U.S. Cl. .................... 534/16; 534/15; 501/152; 501/96.1; 423/21.1; 423/263; 252/301.4 R
[58] Field of Search .................... 534/16, 15; 501/98, 501/152; 423/263, 21.1; 252/301.4 R; 424/1.29

[56] References Cited

U.S. PATENT DOCUMENTS

| 5,332,558 | 7/1994 | Kaneyoshi et al. | 423/21.1 |
| 5,382,452 | 1/1995 | Bruno et al. | 427/215 |
| 5,518,703 | 5/1996 | Dissaux et al. | 423/263 |

FOREIGN PATENT DOCUMENTS

| 0 455 529 | 11/1991 | European Pat. Off. |
| 0 486 351 | 5/1992 | European Pat. Off. |
| 2 018 760 | 10/1979 | United Kingdom. |

OTHER PUBLICATIONS

Journal of Inorganic and Nuclear Chemistry, vol. 26, No. 6, Jun. 1964, pp. 931-936, Barrett et al.

*Primary Examiner*—John Kight
*Assistant Examiner*—Michael G. Hartley
*Attorney, Agent, or Firm*—Wenderoth, Lind & Ponack

[57] ABSTRACT

Disclosed is a method for the preparation of particles of a rare earth ammonium double oxalate by mixing a first aqueous solution of ammonium oxalate and a second aqueous solution of a water-soluble rare earth salt. The double oxalate particles have a polyhedral particle configuration with a uniform particle size distribution, from which a rare earth oxide powder of a polyhedral particle configuration with good flowability can be obtained by calcination, when the first and second aqueous solutions are prepared under exact control of the concentrations of the respective ionic species and the aqueous slurry containing the precipitates of the double oxalate is subjected to an aging treatment during which changes take place in the particle morphology and in the crystallographic structure of the double oxalate particles.

7 Claims, 2 Drawing Sheets

METHOD FOR THE PREPARATION OF POLYHEDRAL PARTICLES OF A RARE EARTH AMMONIUM DOUBLE OXALATE

BACKGROUND OF THE INVENTION

The present invention relates to a method for the preparation of angular or polyhedral particles of a rare earth ammonium double oxalate as a precursor of a rare earth oxide used in a wide field of applications as a base material of various kinds of phosphors, sintering aid of ceramic materials and so on.

It is a well established process for the preparation of a rare earth ammonium double oxalate that an aqueous solution of a water-soluble salt of a rare earth element is admixed with an ammonium compound and oxalic acid or ammonium oxalate so as to precipitate the double oxalate represented by the general formula $NH_4R(C_2O_4)_2 \cdot nH_2O$, in which R is an atom of the rare earth element and n is a positive number. The precipitated particles of the double oxalate, which are separated from the aqueous medium, washed with water, dried and calcined to give a rare earth oxide, may have different particle configuration or morphology depending on the conditions of the precipitation reaction while it is known that the double oxalate as a precursor of a rare earth oxide should desirably have an angular or polyhedral particle configuration.

While rare earth oxides are widely used in various applications, it is desirable that the rare earth oxide particles have a particle configuration and particle size as uniform as possible in order for the rare earth oxide powder to be imparted with greatly enhanced utilizability. In this regard, the method of calcination of a rare earth ammonium double oxalate to give an oxide is a desirable process but this method is not always quite satisfactory with poor reproducibility in respect of the uniformity of the particle configuration and particle size depending on the conditions of the precipitation reaction.

SUMMARY OF THE INVENTION

The present invention accordingly has an object to provide a novel and reliable method for the preparation of particles of a rare earth ammonium double oxalate having a polyhedral particle configuration with good stability and reproducibility.

Thus, the method of the present invention for the preparation of polyhedral particles of a rare earth ammonium double oxalate represented by the general formula $NH_4R(C_2O_4)_2 \cdot nH_2O$, in which R is an atom of the rare earth element selected from the group consisting of yttrium and the elements having atomic numbers in the range from 57 to 71 or a combination thereof and n is a positive number, comprises the steps of:

(a) dissolving ammonium oxalate or a combination of two or all of ammonium oxalate, oxalic acid and ammonia in water to prepare a first aqueous solution with optional addition of an acid other than oxalic acid;

(b) dissolving a water-soluble salt of a rare earth element in water to prepare a second aqueous solution with optional addition of an acid other than oxalic acid;

(c) mixing the first and second aqueous solutions so as to form an aqueous slurry of precipitates;

(d) keeping the aqueous slurry at a temperature in the range from 30° C. to 80° C. for a length of time to effect aging of the precipitates; and (e) separating the precipitates from the aqueous medium, wherein inequalities $$a+b \geq 2d; \quad (I)$$

$$2a-c+e \geq 0.01f; \quad (II)$$

$$2b+c \geq 2d; \text{ and} \quad (III)$$

$$2b+c \geq 2a-c+e, \quad (IV)$$

are satisfied, in which a is the amount of the oxalic acid in moles used in the preparation of the first aqueous solution, b is the amount of the ammonium oxalate in moles used in the preparation of the first aqueous solution, c is the amount of the ammonia in moles used in the preparation of the first aqueous solution, d is the amount of the salt of the rare earth element in moles used in the preparation of the first aqueous solution, e is the total amount of the acid other than oxalic acid in moles used in the preparation of the first and second aqueous solutions and f is the total volume of the first and second aqueous solutions in liters.

In particular, the length of time h in hours for the aging treatment of the precipitates in step (d), which naturally depends on the temperature t in °C. and other factors, is defined by the inequalities:

$$34000 \times \exp\{-8(2a-c+e)/f\} \times \exp(-0.14t) \leq h \leq 60000 \times \exp\{-8(2a-c+e)/f\} \times \exp(-0.14t), \quad (V)$$

in which a, c and e each have the same meaning as defined above. It should be noted that the upper limit of the treatment time h given by the right-hand side of the inequalities is not critical in respect of the product quality but given merely in consideration of the productivity because extension of the treatment time to exceed this upper limit has no particular advantages in the product quality rather with a disadvantage due to the decrease in the productivity.

Preferably, the water-soluble salt of the rare earth element is a chloride or nitrate of the rare earth element and the acid other than oxalic acid optionally added to the first and/or second aqueous solutions should hydrochloric acid or nitric acid, respectively.

DETAILED DESCRIPTION OF THE PREFERRED EMBODIMENTS

Figure 1:
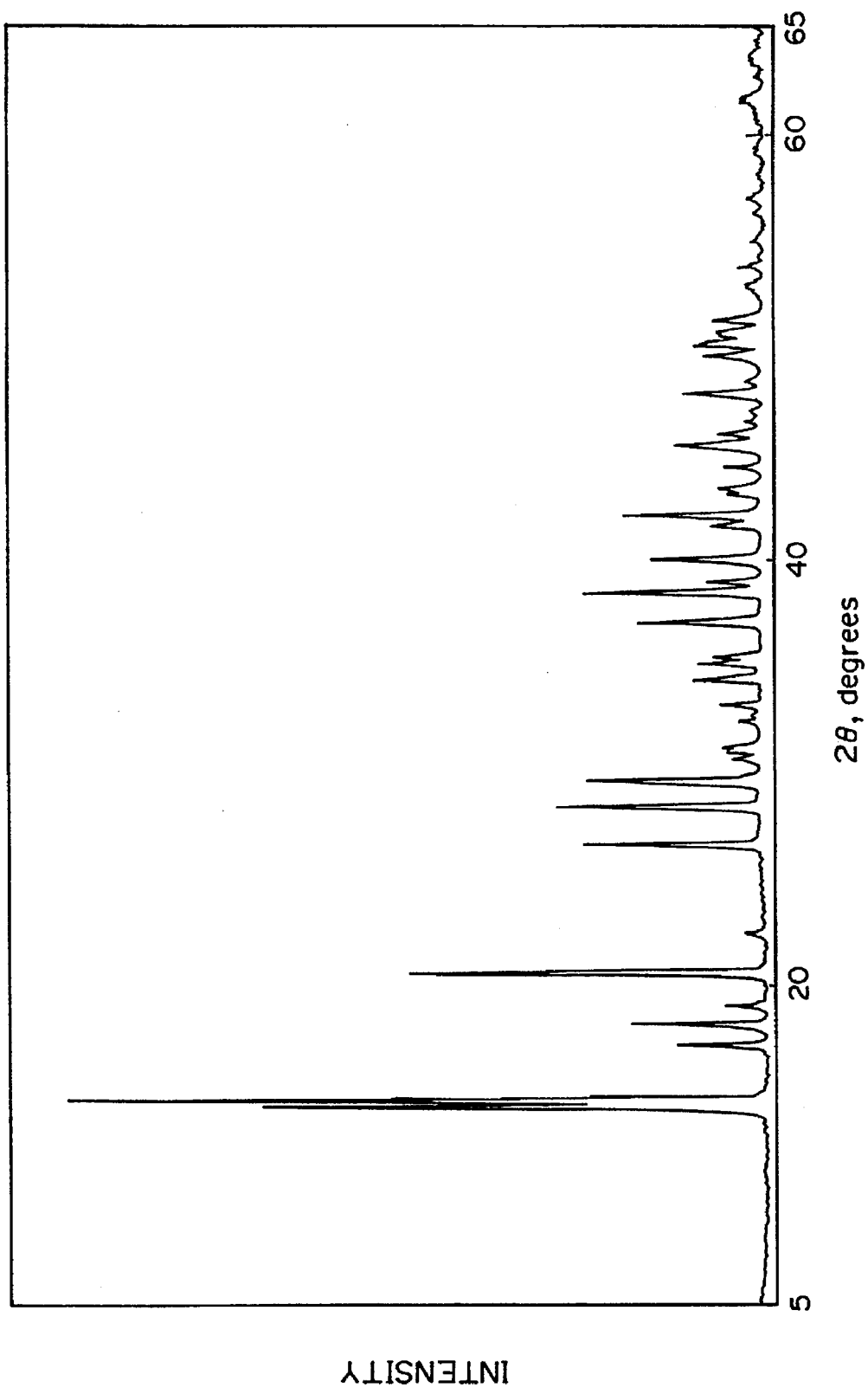
FIGS. 1 and 2 are each an X-ray diffraction diagram of the yttrium ammonium double oxalate particles of the stable type and metastable type, respectively, prepared in the Examples.

In the present invention, it is essential in order to obtain polyhedral particles of a rare earth oxide to first prepare polyhedral particles of a rare earth ammonium double oxalate with stability and in good efficiency, according to the findings obtained by the inventors, by satisfying several requirements 1) that certain relationships are held among the amounts of the rare earth ions, oxalate ions, ammonium ions and hydrogen ions in the reaction mixture including the amounts contained in the liquid phase and the amounts already fixed in the precipitates of the respective ionic species so that it is ensured that the precipitates entirely are in the form of the rare earth ammonium double oxalate, 2) that a certain length of time must be taken for the complete conversion of the double oxalate particles, which are in the form of relatively fine flaky particles in the early stage of the precipitation, into polyhedral particles as a result of an aging effect, and 3) that the conversion of the precipitates into polyhedral particles during the aging process is accelerated by keeping the aqueous medium in an acidic condition.

The most characteristic advantage obtained according to the inventive method consists in that a reproducible method is provided for the preparation of particles of a rare earth ammonium double oxalate having good flowability and a narrow particle size distribution, of which the particles have a polyhedral particle configuration or, namely, a configuration of a rectangular parallelepiped close to a cube, from which polyhedral particles of a rare earth oxide having good flowability and a narrow particle size distribution can be obtained by calcination.

In the first place, a first aqueous solution is prepared by dissolving ammonium oxalate or two or three selected from ammonium oxalate, oxalic acid and ammonia in water. Separately, a second aqueous solution is prepared by dissolving a water-soluble salt, such as chloride and nitrate, of a rare earth element in water. If necessary, an acid other than oxalic acid is added to either one or both of the first and second aqueous solutions.

In the preparation of these aqueous solutions, it is essential that the amounts of the respective compounds dissolved in the solutions and the volume of the solutions are selected or adjusted so that the inequalities given below:

$$a+b \geq 2d; \quad (I)$$

$$2a-c+e \geq 0.01f; \quad (II)$$

$$2b+c \geq 2d; \text{ and} \quad (III)$$

$$2b+c \geq 2a-c+e, \quad (IV)$$

are satisfied, taking the amounts of the oxalic acid, ammonium oxalate and ammonia used in the preparation of the first aqueous solution as a moles, b moles and c moles, respectively, the amount of the water-soluble rare earth salt used in the preparation of the second aqueous solution as d moles, the total amount of the acid other than oxalic acid used in the preparation of the first and second aqueous solutions as e moles and the total volume of the first and second aqueous solutions as f liters. When the optional acid other than oxalic acid is not used, the parameter e is of course equal to 0.

The requirement given by the first inequality (I) is that the molar amount of the oxalate ions $C_2O_4^{2-}$ provided by the oxalic acid and/or ammonium oxalate in the first aqueous solution or, namely, the oxalate ions contained in the liquid phase and already fixed in the solid precipitates as combined after the precipitation reaction must be at least twice of that of the rare earth ions $R^{3+}$ in the second aqueous solution. When this requirement of the inequality (I) is not satisfied, complete conversion of the precipitates into the rare earth ammonium double oxalate can hardly be accomplished. The excess of a+b over 2d should not be unduly large and it is sufficient to have a value of a+b in a slight excess over 2d since an overly increase of a+b over 2d has no particular additional advantages.

The requirement given by the second inequality (II) is that the hydrogen ion concentration in the aqueous medium after mixing of the first and second aqueous solutions is at least 0.01 mole/liter. The requirement given by the third inequality (III) is that the amount of the ammonium ions in the first aqueous solution must be at least twice of that of the rare earth ions in the second aqueous solution. This condition is essential in order for the precipitates to be completely converted into the rare earth ammonium double oxalate.

The requirement given by the fourth inequality (IV) is that the amount of the ammonium ions provided by the first aqueous solution must be equal to or larger than the amount of the hydrogen ions in the aqueous medium after mixing the first and second aqueous solutions. When this requirement is not satisfied, a disadvantage is caused that a part of the rare earth ions is precipitated in the form of a rare earth oxalate $R_2(C_2O_4)_3.nH_2O$ or the rare earth ammonium double oxalate once precipitated in the aqueous medium is partly decomposed into the rare earth oxalate in the course of the aging treatment.

Although these inequalities are not independent each from the others as is readily understood, the respective parameters a, b, c, d, e and f can be freely selected provided that all of these inequalities are satisfied. It has been discovered that these parameters have some influences on the proceeding of the aging effect of the precipitated particles in the aqueous medium for the conversion of the precipitates into polyhedral particles. Assuming an identical temperature of the aging treatment, for example, the time required for the aging treatment is shorter when the acidity of the aqueous medium is higher or, namely, the hydrogen ion concentration therein is higher.

Mixing of the first and second aqueous solution can be performed by introducing the first solution into the second solution or vice versa to give approximately identical results. The length of time taken for completion of mixing of the solutions is not particularly limitative in principle although the time preferably should not exceed 1 hour from the standpoint of controlling the particle diameter of the precipitates. The temperature of the aqueous solutions to be admixed can be room temperature or higher. It is preferable that each of the first and second aqueous solutions is kept at a temperature at or about the same temperature as the temperature of the subsequent aging treatment of the aqueous slurry because the reaction mixture after mixing of the solutions can be rapidly brought to the aging temperature.

After completion of mixing of the first and second aqueous solutions to precipitate the rare earth ammonium double oxalate in the form of an aqueous slurry, the precipitates are subjected to aging by keeping the reaction mixture under agitation at a temperature in the range from 30° to 80° C. Proceeding of aging can be examined microscopically by using an optical microscope for a drop of the slurry periodically taken from the reaction mixture and put on a slide glass plate. While the particles of the double oxalate as precipitated have a fine particle diameter and the particle configuration thereof is irregular or flaky, the particle configuration is gradually changed into a polyhedral form as the aging proceeds to be entirely polyhedral after a sufficiently long time of aging.

Figure 2:
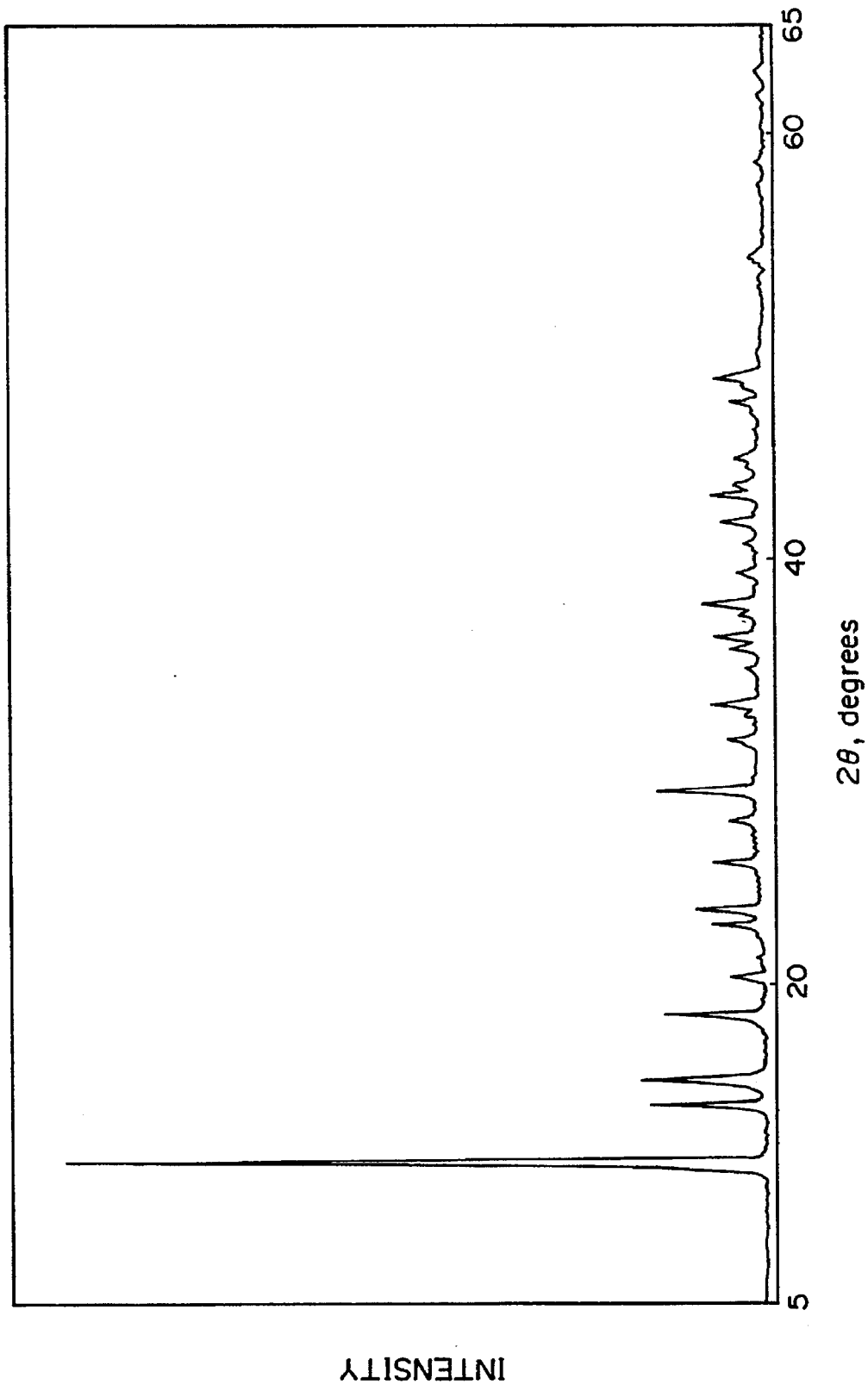

According to the X-ray diffraction diagram shown in FIG. 1 taken for the particles of yttrium ammonium double oxalate immediately after separation from the slurry and washing with water but before heating or drying in Example 1 described later, the yttrium ammonium double oxalate particles in the stage after complete conversion into polyhedral particle configuration have a crystallographic structure identified to be $NH_4R(C_2O_4)_2.H_2O$, referred to hereinafter as the stable type double oxalate, by making reference to the literature data appearing in Journal of Inorganic and Nuclear Chemistry, volume 26, pages 931 to 936 (1964). On the other hand, the crystallographic structure of the oxalate particles as precipitated or still under the aging procedure containing irregular or flaky particles, referred to hereinafter as the metastable type double oxalate, is different from that of the stable type double oxalate as is shown in the X-ray diffraction diagram of FIG. 2 which was taken for the yttrium ammonium double oxalate particles immediately after precipitation at 40° C. Namely, the X-ray diffraction diagram shown in FIG. 2 contains a number of sharp peaks not found in the diagram of FIG. 1 or in the above mentioned literature data. The diffraction peaks characteristic in the metastable type of the double oxalate are also found in the X-ray diffraction diagrams of the particles obtained from the slurry still under the procedure of aging. The above described results suggest that the changes in the morphology and the crystallographic structure of the double oxalate particles are closely correlated to each other.

It has been found that the time taken for the conversion of the irregular or flaky particles into polyhedral form or for the conversion of the metastable form into the stable form as determined by the X-ray diffractometry, referred to as the conversion time hereinafter, is decreased as the temperature of the reaction mixture is increased assuming that the other conditions are identical. Once the stable type of the double oxalate particles have been established, no further growth of the precipitated particles is found even by prolongedly keeping the aqueous slurry at the aging temperature. Assuming that the aging treatment of the aqueous slurry is performed at an identical temperature, the ultimate particle diameter of the precipitated double oxalate is increased as the acidity of the aqueous medium or the hydrogen ion concentration therein is increased. When the aging treatment of the aqueous slurry is to be performed at a temperature different from the temperature in the precipitation reaction, it is sometimes advantageous for the control of the particle size of the desired polyhedral particles that the temperature of the reaction mixture is brought to the temperature of aging as quickly as possible by external heating or cooling or by the addition of a volume of water at a higher or lower temperature although such a temperature-controlling means has no particular effect if undertaken after conversion of a substantial portion of the particles from the metastable type to the stable type which rapidly takes place when the precipitation reaction is performed at a relatively high temperature. Incidentally, the ultimate particle size of the precipitates after complete conversion is smaller when the aging temperature is higher assuming identical conditions of the composition of the reaction mixture. It is essential in the method of the present invention that the aging treatment of the aqueous slurry is performed under agitation until complete conversion of the metastable type into the stable type of the rare earth ammonium double oxalate in order to obtain high uniformity in the particle configuration and a narrow particle size distribution of the double oxalate product which naturally reflect on the particle properties of the rare earth oxide to be obtained by the calcination of the double oxalate. As a measure, the conversion time is given by the inequalities (V) given before.

The polyhedral particles of the rare earth ammonium double oxalate obtained by undertaking the above described precipitation reaction and aging treatment are separated from the aqueous medium by a known method of solid-liquid separation such as filtration and washed with water to be freed from any impurities dissolved in the aqueous medium. The polyhedral particles of the rare earth ammonium double oxalate thus obtained are dried and calcined in air at a temperature of 600° C. or higher, for example, in an electric furnace so that a rare earth oxide powder consisting predominantly of polyhedral particles having a narrow particle size distribution is obtained.

In the following, the method of the present invention is described in more detail by way of examples, which, however, never limit the scope of the invention in any way.

EXAMPLE 1

A first aqueous solution was prepared in a 3-liter beaker by dissolving 0.76 mole of oxalic acid and ammonia water in an amount of 1.44 moles as the ammonium ions in water followed by the addition of an additional volume of water to make up a volume of 1400 ml. The solution was kept at a temperature of 37° C.

Separately, a second aqueous solution was prepared in a 1-liter beaker by dissolving 0.36 mole of yttrium nitrate and 0.72 mole of nitric acid in water followed by the addition of an additional volume of water to make up a volume of 600 ml so that the concentration of the yttrium ions in the solution was 0.60 mole/liter. This second aqueous solution was kept also at a temperature of 37° C.

While keeping the first aqueous solution in the 3-liter beaker at the same temperature under agitation at about 200 rpm of the stirrer revolution, the second aqueous solution was introduced into the 3-liter beaker dropwise taking about 5 minutes to effect the precipitation reaction giving an aqueous slurry at a temperature of 37° C. The aqueous slurry was further agitated at a temperature of 37° C. with a possible deviation of ±1° C. to effect aging of the precipitated particles for 15 hours and the particles were collected by filtration and washed with 2000 ml of water followed by drying to give a powder of yttrium ammonium double oxalate consisting of polyhedral particles. During the period of the aging treatment, drops of the aqueous slurry were taken periodically and microscopically examined on an optical microscope to find that the conversion from the metastable type to the stable type of the particles was still incomplete but already complete at moments 12 hours and 14 hours, respectively, from completion of introduction of the second aqueous solution to the first aqueous solution. The double oxalate particles after establishment of the stable type had a crystallographic structure expressed by the X-ray diffraction diagram shown in FIG. 1.

The yttrium ammonium double oxalate powder was transferred into a porcelain crucible and calcined in an electric furnace at 900° C. for 1 hour in air to give a yttrium oxide powder consisting of polyhedral particles in a yield of at least 99%. The yttrium oxide powder thus obtained was subjected to the laser diffractometric determination of the particle size distribution for the values of $\phi 50$ in $\mu m$ and $\sigma/m$ and measurement of the average particle diameter in $\mu m$ by using a Fischer Subsieve-Sizer to give the results shown in Table 1 below.

The above mentioned parameter $\phi 50$ or, generally, $\phi n$ obtained by the laser diffractometric method is defined as follows. Thus, in the accumulation of the particle volumes starting from the smallest particles, $\phi n$ is given by the particle diameter when n % by volume of the whole particle volume is occupied by the particles having a particle diameter of $\phi$ $\mu m$ or smaller. For example, X $\mu m$ of the $\phi 50$ parameter means that 50% by volume of the whole particles is occupied by the particles having a diameter of X $\mu m$ or smaller. The parameter $\sigma/m$ is correlated to the particle size distribution, in which $\sigma$ is the standard deviation of the distribution and m is the average particle diameter.

EXAMPLE 2

The experimental procedure was substantially the same as in Example 1 except that the first and second aqueous solutions were kept each at a temperature of 45° C. and the temperature of the reaction mixture after completion of mixing of the solutions was brought to 47° C. at which the aging treatment of the aqueous slurry was continued for 2.7 hours before filtration to collect the precipitates. The conversion from the metastable type to the stable type of the double oxalate particles was still incomplete but already complete at moments 2.0 hours and 2.5 hours, respectively, after completion of mixing of the aqueous solutions.

The results of the measurements for the yttrium oxide powder which was obtained by calcination of the double oxalate and consisted of polyhedral particles are shown in Table 1.

EXAMPLE 3

The experimental procedure was substantially the same as in Example 1 except that the first aqueous solution was prepared from 0.04 mole of oxalic acid and 0.72 mole of ammonium oxalate instead of 0.76 mole of oxalic acid and 1.44 moles of ammonia and the first and second aqueous solutions were kept each at a temperature of 60° C. and the temperature of the reaction mixture after completion of mixing of the solutions was brought to 59° C. at which the aging treatment of the aqueous slurry was continued for 0.6 hour before filtration to collect the precipitates. The conversion from the metastable type to the stable type of the double oxalate particles was still incomplete but already complete at moments 0.3 hour and 0.5 hour, respectively, after completion of mixing of the aqueous solutions.

The results of the measurements for the yttrium oxide powder consisting of polyhedral particles are shown in Table 1.

EXAMPLE 4

The experimental procedure was substantially the same as in Example 1 except that the first aqueous solution was prepared from 0.76 mole of ammonium oxalate and 0.46 mole of ammonia instead of 0.76 mole of oxalic acid and 1.44 moles of ammonia, the yttrium nitrate and nitric acid for the second aqueous solution were replaced each with the same molar amount of yttrium chloride and hydrochloric acid, respectively, and the temperatures of the first and second aqueous solutions were 55° C. and 60° C., respectively, so that the reaction mixture after completion of mixing of the solutions had a temperature of 59° C. at which the aging treatment of the aqueous slurry was continued for 3.8 hours before filtration to collect the precipitates. The conversion from the metastable type to the stable type of the double oxalate particles was still incomplete but already complete at moments 3.0 hours and 3.5 hours, respectively, after completion of mixing of the aqueous solutions.

The results of the measurements for the yttrium oxide powder consisting of polyhedral particles are shown in Table 1.

EXAMPLE 5

The experimental procedure was substantially the same as in Example 1 except that the amount of the nitric acid for the second aqueous solution was 0.36 mole instead of 0.72 mole and the temperature of each of the first and second aqueous solutions was 58° C. so that the reaction mixture after completion of mixing of the solutions had a temperature of 58° C. at which the aging treatment of the aqueous slurry was continued for 2.0 hours before filtration to collect the precipitates. The conversion from the metastable type to the stable type of the double oxalate particles was still incomplete but already complete at moments 1.5 hours and 2.0 hours, respectively, after completion of mixing of the aqueous solutions.

The results of the measurements for the yttrium oxide powder consisting of polyhedral particles are shown in Table 1.

EXAMPLE 6

The experimental procedure was substantially the same as in Example 5 except that the amount of the ammonia for the first aqueous solution was 1.08 moles instead of 1.44 moles and the temperatures of the first and second aqueous solutions were 39° C. and 36° C., respectively, so that the reaction mixture after completion of mixing of the solutions had a temperature of 37° C. at which the aging treatment of the aqueous slurry was continued for 8.5 hours before filtration to collect the precipitates. The conversion from the metastable type to the stable type of the double oxalate particles was still incomplete but already complete at moments 6.0 hours and 8.0 hours, respectively, after completion of mixing of the aqueous solutions.

The results of the measurements for the yttrium oxide powder consisting of polyhedral particles are shown in Table 1.

EXAMPLE 7

The experimental procedure was substantially the same as in Example 1 except that the amount of the ammonia for the first aqueous solution was 1.06 moles instead of 1.44 moles, the second aqueous solution was prepared from the same molar amount of yttrium chloride instead of yttrium nitrate and 0.12 mole of hydrochloric acid instead of 0.72 mole of nitric acid and the temperatures of the first and second aqueous solutions were 45° C. and 48° C., respectively, so that the reaction mixture after completion of mixing of the solutions had a temperature of 47° C. at which the aging treatment of the aqueous slurry was continued for 8.0 hours before filtration to collect the precipitates. The conversion from the metastable type to the stable type of the double oxalate particles was still incomplete but already complete at moments 5.5 hours and 7.0 hours, respectively, after completion of mixing of the aqueous solutions.

The results of the measurements for the yttrium oxide powder consisting of polyhedral particles are shown in Table 1.

EXAMPLE 8

The experimental procedure was substantially the same as in Example 1 except that the amount of the ammonia for the first aqueous solution was 0.84 mole instead of 1.44 moles, the amount of the nitric acid for the second aqueous solution was 0.12 mole instead of 0.72 mole and the temperature of each of the first and second aqueous solutions was 50° C. so that the reaction mixture after completion of mixing of the solutions had a temperature of 48° C. at which the aging treatment of the aqueous slurry was continued for 2.2 hours before filtration to collect the precipitates. The conversion from the metastable type to the stable type of the double oxalate particles was still incomplete but already complete at moments 1.5 hours and 2.0 hours, respectively, after completion of mixing of the aqueous solutions.

The results of the measurements for the yttrium oxide powder consisting of polyhedral particles are shown in Table 1.

EXAMPLE 9

The experimental procedure was substantially the same as in Example 1 except that the first aqueous solution was prepared from 0.06 mole of oxalic acid and 0.70 mole of ammonium oxalate instead of 0.76 mole of oxalic acid and 1.44 moles of ammonia, nitric acid was not added to the second aqueous solution and the temperature of each of the first and second aqueous solutions was 60° C. so that the reaction mixture after completion of mixing of the solutions had a temperature of 60° C. at which the aging treatment of the aqueous slurry was continued for 6.0 hours before filtration to collect the precipitates. The conversion from the metastable type to the stable type of the double oxalate particles was still incomplete but already complete at moments 5.0 hours and 6.0 hours, respectively, after completion of mixing of the aqueous solutions.

The results of the measurements for the yttrium oxide powder consisting of polyhedral particles are shown in Table 1.

EXAMPLE 10

The experimental procedure was substantially the same as in Example 1 except that the yttrium nitrate was replaced with the same molar amount of gadolinium nitrate and the temperatures of each of the first and second aqueous solutions were 45° C. and 46° C., respectively, so that the reaction mixture after completion of mixing of the solutions had a temperature of 46° C. at which the aging treatment of the aqueous slurry was continued for 4.2 hours before filtration to collect the precipitates. The conversion from the metastable type to the stable type of the double oxalate particles was still incomplete but already complete at moments 3.3 hours and 4.0 hours, respectively, after completion of mixing of the aqueous solutions.

The results of the measurements for the gadolinium oxide powder consisting of polyhedral particles are shown in Table 1.

Comparative Example 1

The experimental procedure was substantially the same as in Example 1 except that the yttrium nitrate and nitric acid were replaced each with the same molar amount of yttrium chloride and hydrochloric acid, respectively, and the temperature of each of the first and second aqueous solutions was 35° C. followed by increase of the temperature of the reaction mixture after completion of mixing of the solutions 38° C. at which the aging treatment of the aqueous slurry was continued for 6.2 hours, when conversion of the metastable type to the stable type of the double oxalate particles was still incomplete, before filtration to collect the precipitates.

The results of the measurements for the yttrium oxide powder, which consisted of a combination of relatively large polyhedral particles and fine platelet-like particles, are shown in Table 1.

Comparative Example 2

The experimental procedure was substantially the same as in Example 2 except that the aqueous slurry of the double oxalate precipitates was filtered after 0.1 hour of aging, when conversion of the metastable type to the stable type of the double oxalate particles had little proceeded, to collect the precipitates.

The results of the measurements for the yttrium oxide powder, which consisted of agglomerate particles of irregular configuration, are shown in Table 1.

Comparative Example 3

The experimental procedure was substantially the same as in Example 1 except that the first aqueous solution was prepared from 0.24 mole of oxalic acid and 0.52 mole of ammonium oxalate instead of 0.76 mole of oxalic acid and 1.44 moles of ammonia, the temperatures of the first and second aqueous solutions were 42° C. and 41° C., respectively, so that the temperature of the reaction mixture after completion of mixing of the solutions was 41° C. and the aqueous slurry of the double oxalate precipitates was filtered after 4.0 hours of aging at 40° C., when the double oxalate precipitates consisted mainly of rod-like particles, to collect the precipitates.

The results of the measurements for the yttrium oxide powder, which consisted of rod-like particles, are shown in Table 1.

Comparative Example 4

The experimental procedure was substantially the same as in Example 1 except that the first aqueous solution was prepared from 0.04 mole of oxalic acid and 0.72 mole of ammonium oxalate instead of 0.76 mole of oxalic acid and 1.44 moles of ammonia, the amount of nitric acid added to the second aqueous solution was 1.41 moles instead of 0.72 mole, the temperature of each of the first and second aqueous solutions was 40° C. so that the temperature of the reaction mixture after completion of mixing of the solutions was 40° C. and the aqueous slurry of the double oxalate precipitates was filtered after 5.0 hours of aging at 40° C. The double oxalate particles after 4.0 hours of aging mainly had a rod-like configuration and the X-ray diffraction diagram contained diffraction peaks which could be identified to belong to yttrium oxalate of the formula $Y_2(C_2O_4)_3 \cdot 9H_2O$.

The results of the measurements for the yttrium oxide powder, which consisted of rod-like particles, are shown in Table 1.

Comparative Example 5

The experimental procedure was substantially the same as in Example 1 except that the amount of the ammonia for the first aqueous solution was 0.66 mole instead of 1.44 moles, the second aqueous solution was prepared from the same molar amount of yttrium chloride and 0.06 mole of hydrochloric acid instead of 0.72 mole of nitric acid, the temperatures of the first and second aqueous solutions were 39° C. and 41° C., respectively, so that the temperature of the reaction mixture after completion of mixing of the solutions was 40° C. at which aging of the aqueous slurry of the double oxalate precipitates was performed for 4.5 hours before filtration of the aqueous slurry. The double oxalate particles after 4.0 hours of aging mainly had a rod-like configuration.

The results of the measurements for the yttrium oxide powder der, which consisted of rod-like particles, are shown in Table 1.

Comparative Example 6

The experimental procedure was substantially the same as in Example 1 except that the first aqueous solution was prepared from 0.76 mole of ammonium oxalate and 0.72 mole of ammonia instead of 0.76 mole of oxalic acid and 1.44 moles of ammonia, the temperatures of the first and second aqueous solutions were 54° C. and 49° C., respectively, and the temperature of the reaction mixture after completion of mixing of the solutions was brought to 60° C. at which aging of the aqueous slurry of the double oxalate precipitates was performed for 6 hours before filtration of the aqueous slurry. The double oxalate particles after 5.5 hours of aging mainly had a fine and flaky particle configuration.

The results of the measurements for the yttrium oxide powder, which consisted of agglomerate particles of irregular configuration, are shown in Table 1.

TABLE 1

| | φ50, μm | σ/m | Particle diameter, μm |
|---|---|---|---|
| Example | | | |
| 1 | 7.66 | 0.32 | 2.60 |
| 2 | 4.68 | 0.31 | 1.60 |
| 3 | 3.58 | 0.28 | 1.15 |
| 4 | 2.54 | 0.27 | 0.90 |
| 5 | 2.45 | 0.27 | 0.85 |
| 6 | 7.10 | 0.33 | 2.45 |
| 7 | 4.34 | 0.31 | 1.30 |
| 8 | 5.29 | 0.32 | 1.70 |
| 9 | 2.15 | 0.24 | 0.95 |
| 10 | 4.50 | 0.34 | 1.50 |
| Comparative Example | | | |
| 1 | 6.07 | 0.58 | 1.45 |
| 2 | 3.48 | 0.54 | 1.00 |
| 3 | 8.86 | 0.42 | 1.65 |
| 4 | 9.22 | 0.44 | 1.75 |
| 5 | 9.03 | 0.44 | 1.70 |
| 6 | 3.36 | 0.48 | 0.95 |

What is claimed is:

1. A method for the preparation of polyhedral particles of a rare earth ammonium double oxalate represented by the general formula $NH_4R(C_2O_4)_2 \cdot nH_2O$, in which R is an atom of a rare earth element selected from the group consisting of yttrium and the elements having atomic numbers in the range from 57 to 71 or a combination thereof and n is a positive number, which consists essentially of the steps of:

(a) dissolving, in water, (1) ammonium oxalate or (2) two or three compounds selected from the group consisting of ammonium oxalate, oxalic acid and ammonia to prepare a first aqueous solution;

(b) dissolving a water-soluble salt of a rare earth element in water to prepare a second aqueous solution;

(c) mixing the first and second aqueous solutions so as to form an aqueous slurry of precipitates;

(d) keeping the aqueous slurry containing the precipitates at a temperature in the range from 30° C. to 80° C. to effect aging of the precipitates; and (e) separating the precipitates from the aqueous medium, wherein inequalities:

$a+b \geq 2d$;

$2a-c \geq 0.01f$;

$2b+c \geq 2d$; and $2b+c \geq 2a-c$, are satisfied, in which a is the amount of the oxalic acid in moles used in the preparation of the first aqueous solution, b is the amount of the ammonium oxalate in moles used in the preparation of the first aqueous solution, c is the amount of the ammonia in moles used in the preparation of the first aqueous solution, d is the amount of the salt of the rare earth element in moles used in the preparation of the first aqueous solution and f is the total volume of the first and second aqueous solutions in liters.

2. A method for the preparation of polyhedral particles of a rare earth ammonium double oxalate represented by the general formula $N_4R(C_2O_4)_2 \cdot nH_2O$, in which R is an atom of the rare earth element selected from the group consisting of yttrium and the elements having atomic numbers in the range from 57 to 71 or a combination thereof and n is a positive number, which consists essentially of the steps of:

(a) dissolving, in water, (1) ammonium oxalate or (2) two or three compounds selected from the group consisting of ammonium oxalate, oxalic acid and ammonia in water to prepare a first aqueous solution;

(b) dissolving a water-soluble salt of a rare earth element in water to prepare a second aqueous solution;

(c) mixing the first and second aqueous solutions so as to form an aqueous slurry of precipitates;

(d) keeping the aqueous slurry at a room temperature in the range from 30° C. to 80° C. to effect aging of the precipitates; and (e) separating the precipitates from the aqueous medium, either one or both of the first and second aqueous solutions being admixed with an acid other than oxalic acid, wherein inequalities:

$a+b \geq 2d$;

$2a-c+e \geq 0.01f$;

$2b+c \geq 2d$; and $2b+c \geq 2a-c+e$, are satisfied, in which a is the amount of the oxalic acid in moles used in the preparation of the first aqueous solution, b is the amount of the ammonium oxalate in moles used in the preparation of the first aqueous solution, c is the amount of the ammonia in moles used in the preparation of the first aqueous solution, d is the amount of the salt of the rare earth element in moles used in the preparation of the first aqueous solution, e is the amount of the acid other than oxalic acid in moles used in the preparation of the first and second aqueous solutions and f is the total volume of the first and second aqueous solutions in liters.

3. The method for the preparation of polyhedral particles of a rare earth ammonium double oxalate as claimed in claim 1 in which the water-soluble salt of the rare earth element is a chloride or nitrate of the rare earth element.

4. The method for the preparation of polyhedral particles of a rare earth ammonium double oxalate as claimed in claim 2 in which the water-soluble salt of the rare earth element is a chloride of the rare earth element and the acid other than oxalic acid is hydro-chloric acid.

5. The method for the preparation of polyhedral particles of a rare earth ammonium double oxalate as claimed in claim 2 in which the water-soluble salt of the rare earth element is a nitrate of the rare earth element and the acid other than oxalic acid is nitric acid.

6. The method for the preparation of polyhedral particles of a rare earth ammonium double oxalate as claimed in claim 1 in which the aging of the precipitates in step (d) is performed for a length of time defined by the inequalities:

$34000 \times \exp\{-8(2a-c)/f\} \times \exp(-0.14t) \leq h \leq 60000 \times \exp\{-8(2a-c)/f\} \times \exp(-0.14t)$, in which h is the length of time in hours, t is the temperature of the aqueous slurry in °C. and a and c each have the same meaning as defined above.

7. The method for the preparation of polyhedral particles of a rare earth ammonium double oxalate as claimed in claim 2 in which the aging of the precipitates in step (d) is performed for a length of time defined by the inequalities:

$34000 \times \exp\{-8(2a-c+e)/f\} \times \exp(-0.14t) \leq h \leq 60000 \times \exp\{-8(2a-c+e)/f\} \times \exp(-0.14t)$, in which h is the length of time in hours, t is the temperature of the aqueous slurry in °C. and a, c and e each have the same meaning as defined above.

* * * * *